United States Patent [19]

Young

[11] Patent Number: 4,968,618

[45] Date of Patent: Nov. 6, 1990

[54] COMPOSITION AND METHOD FOR PROMOTING GROWTH OF GRANULOCYTES

[75] Inventor: Michael Young, Gainesville, Fla.

[73] Assignee: University of Florida, Gainesville, Fla.

[21] Appl. No.: 282,500

[22] Filed: Dec. 12, 1988

Related U.S. Application Data

[63] Continuation of Ser. No. 672,360, Nov. 16, 1984, abandoned.

[51] Int. Cl.$^5$ .................. C12N 5/00; C07K 15/06
[52] U.S. Cl. .................. 435/240.21; 530/351; 435/240.3
[58] Field of Search .......... 435/240.21, 240.3, 240.31, 435/240.25; 530/351

[56] References Cited

U.S. PATENT DOCUMENTS

| | | | |
|---|---|---|---|
| 4,185,095 | 1/1980 | Young | 424/95 |
| 4,287,184 | 9/1981 | Young | 514/21 |
| 4,407,744 | 10/1983 | Young | 530/399 |
| 4,621,050 | 11/1986 | Sugimoto | 435/68 |

OTHER PUBLICATIONS

Gee et al., *Proc. Nat'l. Acad. Sci.* U.S.A., 80(23): 7215–7218 (Dec. 1983).

Young et al, Biochemistry, vol. 17, No. 8, 1978, pp. 1490–1498.

Iscove et al, Blood, vol. 37, No. 1, Jan. 1971, pp. 1–5.

Thomas et al, Methods in Enzymology, vol. 80, pp. 609–620.

*Primary Examiner*—Elizabeth C. Weimar
*Attorney, Agent, or Firm*—Kerkam, Stowell, Kondracki & Clarke

[57] ABSTRACT

A composition and method for stimulating the growth of human granulocytes based upon the G-CSF activity of mouse nerve growth factor (NGF).

7 Claims, 4 Drawing Sheets

COMPOSITION AND METHOD FOR PROMOTING GROWTH OF GRANULOCYTES

This is a continuation of application Ser. No. 672,360, filed Nov. 16, 1984, now abandoned.

BACKGROUND OF THE INVENTION

1. Field of the Invention

The present invention relates to the promotion of the growth of granulocytes from human bone marrow utilizing nerve growth factor.

2. The Prior Art

Recently a nerve growth factor was derived from mouse saliva and mouse submandibular glands, which is characterized by its high degree of stability in dilute aqueous solutions and a molecular weight of 116,000 (Orenstein et al (1978) Proc. Natl. Acad. Sci., U.S.A. 75, 5497–5000, U.S. Pat. Nos. 4,185,095 and 4,407,744). The factor has several uses, i.e., plasminogen activator (U.S. Pat. No. 4,185,095), neurite outgrowth stimulator (U.S. Pat. No. 4,185,095), wound healing (U.S. Pat. No. 4,281,184; Li et al (1980) Proc. Natl. Acad. Sci., U.S.A. 77, 4379–4381), substitutes enzymically for the first component of complement (Boyle et al (1982) Proc. Natl. Acad. Sci., U.S.A. 79, 2519–2522), leukocyte chemotaxis mediator (Lawman et al (1984) J. Immunol. Methods, 69, 197–205; Boyle et al (1984) J. Immunol., in press; and Gee et al (1983) Proc. Natl. Acad. Sci., U.S.A. 80, 7215–7218). An antibody to the mouse nerve growth factor has also been elicited (U.S. Pat. No. 4,230,691).

This mouse derived nerve growth factor (NGF) has a molecular weight of 116,000, contains 1 gram-atom of tightly bound Zn(II) per mole (Young et al (1980) Biochemistry 19, 5316–5321; Pattison et al (1975) Biochemistry 14, 2733–2739), and consists of three different subunits, termed $\alpha$, $\beta$, and $\gamma$ (Varon et al (1967) Biochemistry 7, 1926–1303). The $\beta$-subunit is responsible for promoting neurite outgrowth from sympathetic and embryonic sensory ganglia (Levi-Montancini et al (1968) Physiol. Rev. 48, 534–569; Bocchini et al (1969) Proc. Natl. Acad. Sci. U.S.A. 64, 787–794). The $\gamma$-subunit is a member of the serine class of proteolytic enzymes (Orenstein et al, supra; Thomas et al (1981) J. Biol. Chem. 256, 9156–9166), and displays a highly restricted substrate specificity towards certain lysyl and argininyl peptide bonds (Orenstein et al, supra; Greene et al (1968) Proc. Natl. Acad. Sci. U.S.A. 60, 1383–1388). The $\alpha$-subunit has no known function. Recent studies have shown that the subunit structural formula for NGF is $\alpha_2\beta\gamma$ (Young et al, supra). The molecular weight of all of the subunits lie in the range 26,000–28,000.

In an area of research totally unrelated to nerve growth factor, several agents have been discovered which stimulate growth of granulocyte colonies from primitive bone marrow stem cells. Known granulocyte colony-stimulating factors (G-CSF) include those disclosed by Metcalf et al (1983) J. Cell. Physiol. 116, 198–206; Nicola et al (1983) J. Biol. Chem. 258, 9017–9023 and Burgess et al (1977) J. Biol. Chem. 252, 1998–2003.

The mouse lung-derived granulocyte stimulating factor (Nicola et al, supra) is a glycoprotein of molecular weight 25,000 and contains internal disulfide bonds. Mouse lung G-CSF exhibits half-maximal activity upon normal mouse marrow cells at $3 \times 10^{-12}$M. Whether it possesses a protease activity is not known. At low concentrations, this G-CSF stimulates only granulocyte colony-forming cells. At higher concentrations it promotes the growth of mixed macrophage plus granulocyte colonies, as well as small numbers of macrophage colonies.

The known G-CSF factors are obtainable only in extremely small amounts thereby greatly limiting the avenues of research necessary to establish practical therapeutic and diagnostic applications for these agents. For example, research on the normal granulocyte maturation process as well as in pathologic states such as leukemia wherein the maturation process is altered would be greatly facilitated by the ready availability of large amounts of a G-CSF.

It is an object of the present invention to provide a novel composition and method for stimulating the growth of granulocytes from primitive bone marrow stem cells which are based upon factors possessing heretofore undiscovered G-CSF activities which are readily obtainable in large amounts.

SUMMARY OF THE INVENTION

The present invention is based upon the discovery that NGF or its $\gamma$-subunit exhibits G-CSF activity in human bone marrow.

The present invention embodies a composition for stimulating the growth of granulocytes from human bone marrow cells comprising an admixture of a granulocyte stimulating effective amount of NGF or its $\gamma$-subunit and a nutrient medium for human granulocyte proliferation.

The invention also embodies the above-described composition additionally containing human bone marrow.

The invention further embodies a method for the promotion of growth of granulocytes from human bone marrow cells comprising contacting human bone marrow cells with a granulocyte stimulating effective amount of NGF or its $\gamma$-subunit in the presence of nutrients for the proliferation of human granulocytes for a time sufficient to stimulate the proliferation of granulocytes.

DETAILED DESCRIPTION OF THE INVENTION

It is highly surprising that NGF and its $\gamma$-subunit display multiple biological activities in such disparate physiological areas as neurite outgrowth stimulation, proteolytic activity, wound healing and, most unexpectedly, G-CSF activity.

In addition to its long-recognized effects upon certain segments of the automatic and sensory nervous system (Levi-Montalcini (1982) Ann. Rev. Neurosci. 5, 341–362), NFG displays several other biological activities that arise from the proteolytic activity of its $\gamma$-subunit: (i) It can activate plasminogen with subsequent plasmin-mediated lysis of a fibrin clot (Orenstein et al, supra); (ii) it can substitute enzymically for the first (and only the first) component of complement (CI) in activating the classical complement pathway, an activity that can be regulated by the human serum CI-inactivator protein (Boyle et al, supra); (iii) NGF has been shown to be chemotactic for polymorphonuclear leukocytes in vivo (Lawman et al, supra); Boyle et al (1984), supra). In addition to the above proteolytically-mediated activities, NGF is also hemotactic for polymorphonuclear leukocytes in vitro, and this property is independent of its protease activity (Gee et al, supra). Taken together, the preceding non-neuronal activities of NGF are relevant to some of the cellular and chemical events associated with the early inflammatory response to injury. This may explain in part the observation (Li et al, supra) that NGF can accelerate the rate of healing of experimentally-induced wounds in mice.

The crux of the present invention resides in the discovery that, unexpectedly, NGF and its γ-subunit are potent colony-stimulating factors for human bone marrow granulocyte progenitor cells (G-CSF). Only granulocyte-containing colonies are formed in the presence of NGF at concentrations as low as $9 \times 10^{-12}$. Most unexpectedly, macrophage colonies are absent. The G-CSF activity of NGF arises from its single γ-subunit, but it is not dependent upon the serine protease activity of this subunit.

Concentrations of NGF or its γ-subunit between about $10^{-11}$M and about $10^{-9}$M are sufficient to stimulate the growth of granulocytes from human bone marrow cells.

Complete inactivation of the proteolytic activity of NGF as well as that of the purified γ-subunit has no significant effect on the G-CSF activity.

NGF and its γ-subunit may be isolated and purified according to the methods described in U.S. Pat. No. 4,185,095; Young et al (1978) Biochemistry 17, 1490–1498; Thomas et al (1981) Meth. Enzymol. 80, 609–620, the disclosure of all of which are incorporated herein by reference.

The nutrient medium in which the NGF, the γ-subunit and, optionally, the human bone marrow, are incorporated may comprise any of those conventionally used for the proliferation of human granulocytes. See Iscove et al, Blood, Vol. 37, pp. 1–5 (1971), the disclosure of which is incorporated herein by reference.

The G-CSF factors known heretofore are available only in minute amounts thereby drastically limiting the amount of research that could be accomplished therewith. NGF and its γ-subunit may be inexpensively prepared and purified in very large amounts thereby permitting a widening of the scope of research therewith. For example, studies on the normal granulocyte maturation process and in areas of pathologic states such as leukemia wherein the maturation process is altered are now possible because of the present invention.

The invention is illustrated by the following non-limiting examples:

EXAMPLE 1

NGF was purified from male mouse submandibular glands as described by Young et al (1978), supra. All preparations thereof were shown to be electrophoretically homogenous by polyacrylamide gel staining and by radioimmuno-assay of serial gel slices (Young et al (1978), supra; Orenstein et al, supra). DIP-NGF was prepared and described by Young et al (1980), supra. MK-NGF was prepared by reaction of the active site affinity inhibitor D-phe-pro-arg chloromethyl ketone $(6.4 \times 10^{-5}M)$ with NGF $(3.7 \times 10^{-6}M)$ for two hours at 25° with 0.1M Tris.HCl, 0.02M EDTA, pH7.5, as solvent. After thorough dialysis against 0.1M Tris.HCl pH7.5 to remove reagents, both DIP-NGF and MK-NGF displayed <0.1% residual enzymic activity compared to native NFG, when measured spectrophotometrically ($\lambda=410$ nm) with BAPNA as substrate (Erlanger et al (1961) Arch. Biochem. Biophys. 95, 271–278). The three subunits of NGF were isolated and purified from the parent molecule by carboxymethylcellulose chromatography (Thomas et al, supra). Concentrations of NGF were measured spectrophotometrically ($\lambda=280$ nm) (Lawman et al, supra).

Bone marrow samples were obtained from a total of 19 donors. Of these marrows, 13 were from patients with acute leukemia (one myelomoncytic, 12 lymphoblastic), all in hematologic remission. Five marrow samples were obtained from patients with non-hematologic malignancies. Previous studies have shown that marrow cells from leukemic individuals as well as normal marrow cells, are absolutely dependent upon CSF for proliferative activity, and that the concentration-response curves are essentially normal (Metcalf (1982) Cancer Inst. Monogr. 60, 123–131; Gross et al (1984) Am. J. Hematol. 16, 325–333). The method used for measurement of bone marrow colony formation was a modification of the procedure of Iscove et al (1971 Blood 37, pp. 1–5. The mononuclear fraction of bone marrow was prepared by Ficollhypaque density gradient centrifugation, washed three times with MEM (plus glutamine) (Givco), and resuspended in MEM to a concentration of $2.2 \times 10^6$ cells/ml. One milliliter of cells, containing (v/v) 0.7% methylcellulose (Dow Chemical Co., Cleveland, Ohio), 20% fetal calf serum (Gibco), and $2 \times 10^5$ cells/ml was plated into $35 \times 10$ mm tissue culture dishes. For NGF assays, 100 μl of a solution of NGF in MEM plus 0.9 ml of the above medium containing $2 \times 10^5$ cells/ml was plated. Cultures were incubated at 37° in humidified air plus 5° $CO_2$ for 14 days. Colonies containing >40 cells were counted microscopically. To serve as a positive control for colony growth, media conditioned for 7 days by peripheral human blood leukocytes was prepared and used as a source of colony-stimulating activity as described by Iscove et al, supra.

FIG. 1 illustrates a representative colony-growth vs time plot for NGF at a concentration of 0.1 μg/ml. As shown, NGF stimulates significant colony growth, which reaches a maximum plateau level after 11–12 d in culture. Culture control plates (in the absence of NFG) always contained fewer than 10 colonies per plate after 14 d incubation). A particularly striking feature of the colony growth pattern shown in FIG. 1 was the absence of macrophage colonies as well as of mixed granulocyte-macrophage colonies. Only granulocyte colonies were observed at all time intervals of culture. Microscopic study of stained (Wright-Giemsa) colonies demonstrated cells in various stages of differentiation along the granulocyte maturation pathway. After 11-4 d in culture, colonies ranged in size from 50–200 cells per colony.

To minimize the possibility that the NGF preparations were contaminated with a small amount of an unrecognized non-NGF impurity, 40 μg of NGF was analyzed by polyacrylamide gel electrophoresis under non-denaturing solvent conditions (Orenstein et al, supra). One gel was stained (Coomassie blue) to locate the NGF-containing zone; a second gel was sliced and the slices were eluted with 0.1M Tris.HCl, pH 7.5. The resulting solutions were examined in the colony-growth assay described above. FIG. 2 shows that only the zone corresponding precisely to the electrophoretic mobility of NGF stimulated granulocyte colony growth.

EXAMPLE 2

As noted above, NGF is a member of the serine-class of proteolytic enzymes. To evaluate the potential role of this enzymic property in the mechanism of NFG-stimulated granulocyte colony growth, both DIP-NGF and NGF inactivated by reaction with D-phe-pro-arg-chloromethyl ketone (MK-NGF) were prepared. These two enzymically inactive derivatives were chosen because the mechanisms of inactivation are different. iPr$_2$P-F irreversibly inactivates the serine protease family of enzymes by reaction with the active site serine, whereas the chloromethyl ketone reacts irreversibly with a specific active-site histidine residue (Kettner et al (1980) Arch. Biochem. Biophys. 202, 420–430. The procedure of Example 1 was repeated with the inactivated NGF's. FIG. 1 shows that both of these enzymically inactive NGF derivatives yield kinetic growth curves that are closely similar to that of NGF. (The slightly lower colony growth produced by DIP-NFG and MK-NFG is barely outside of experimental error). Thus it can be concluded that elimination of the protease activity of NGF has no appreciable effect upon its G-CSF activity.

EXAMPLE 3

Examples 1 and 2 were repeated utilizing different concentrations of NGF or derivative thereof.

FIG. 3 illustrates concentration-response profiles for native NGF, as well as for its two proteolytically-inactivated derivatives. For all three proteins, colony-stimulating activity was observed at concentrations as low as $8.6 \times 10^{-12}$M, with maximal activity near $8.6 \times 10^{-10}$M. The peak activities of the protease inactive derivatives appeared to be slightly lower than that of NGF, although again these differences possess little or no statistical significance. The data shown in FIG. 3, like those in FIG. 1, further demonstrate that elimination of the enzymic activity of NGF has no effect upon its granulocyte colony-stimulating activity.

EXAMPLE 4

To establish which of the three subunits of NGF might be responsible for its G-CSF activity, the $\alpha$, $\beta$, and $\gamma$ subunits were purified from NGF by ion exchange chromatography (Thomas et al, supra). The procedure of Example 1 was repeated utilizing the subunits of NGF. The results illustrated in FIG. 4 demonstrate that of the three, only the $\gamma$-subunit displays G-CSF activity in this assay system. Furthermore, as with NGF itself, inactivation of the proteolytic activity of the $\gamma$-subunit by reaction with the active site-directed chloromethyl ketone (MK-$\gamma$, FIG. 4) has no effect upon its colony-stimulating activity. For comparison with NGF and its $\gamma$-subunit, FIG. 4 also illustrates the extent of colony growth stimulated by the colony-stimulating factor(s) obtained from leukocyte-conditioned media (Iscove et al, supra). In contrast to NGF, leukocyte-conditioned medium produced growth of both granulocyte as well as monocyte-containing colonies in a ratio of 4:1, respectively. FIG. 3 presents the concentration response profile for the $\gamma$-subunit, which like the parent NGF molecule, exhibits maximal activity at concentrations close to 1 nM. This result is fully consistent with the finding that one molecule of NGF contains one molecule of $\gamma$-subunit.

The above examples demonstrate that the high molecular weight form of mouse submandibular gland NGF promotes growth of pure granulocyte colonies by stimulation of human myeloid progenitor cells. Maximal activity in this system occurs at an NGF concentration of $8.6 \times 10^{-10}$M, and it does not depend upon the proteolytic activity of the molecule.

The G-CSF activity of NGF resides within and is a property of its $\gamma$-subunit. Moreover, like the enzymically inactive derivatives of NGF itself, inactivation of the serine protease activity of this subunit has no effect upon its G-CSF activity.

The prior art indicates that hematopoietic cell proliferation is controlled by the actions of a family of colony-stimulating factors. At least four classes of these are recognized. They include a macrophage colony-stimulating factor (Stanley et al (1977), J. Bio. Chem. 252, 4305–4312), a G-CSF (Metcalf et al, supra; Nicola et al, supra), a granulocyte plus macrophage colony stimulating factor (GM-CSF) (Burgess et al, supra) and interleukin-3 that promotes the growth of a variety of myeloid progenitor cells (Ihle et al (1983) J. Immunol. 131, 282–287).

The molecular properties of the G-CSF isolated from mouse lung-conditioned medium (Nicola et al, supra) were compared with those of the $\gamma$-subunit. The lung derived factor exhibits half-maximal activity upon normal mouse cells at $3 \times 10^{-12}$M. At low concentrations this G-CSF stimulates only granulocyte colony-forming cells. At higher concentrations it promotes the growth of mixed macrophage plus granulocyte colonies, as well as small numbers of macrophage colonies (Metcalf et al, supra).

With human marrow cells, the $\gamma$-subunit of NGF exhibits half-maximal activity close to $1.6 \times 10^{-11}$M (FIG. 3). At all concentrations studies, the $\gamma$-subunit of NGF promotes the growth only of granulocyte colonies.

The reason why mouse submandibular gland NGF contains a subunit that can stimulate growth and differentiation of human bone marrow progenitor cells is not clear. However, NGF has the capacity to accelerate the overall process of wound healing as well as to operate upon certain cellular and chemical processes associated with the early inflammatory response to injury. For example, it can activate plasminogen, substitute enzymically for the first component of complement, and mediate leukocyte chemotaxis, both in vitro and in vivo. While not desiring to be bound by any theory as to the mechanism of the invention it may be that the G-CSF activity of the NGF plays a role in the promotion of granulopoiesis, secondary to the development of an inflammatory reaction.

It will be understood by those skilled in the art that, by the term NGF is meant any $\gamma$-subunit containing nerve growth factor derived from any vertebrate animal species, including humans.

Figure 1:
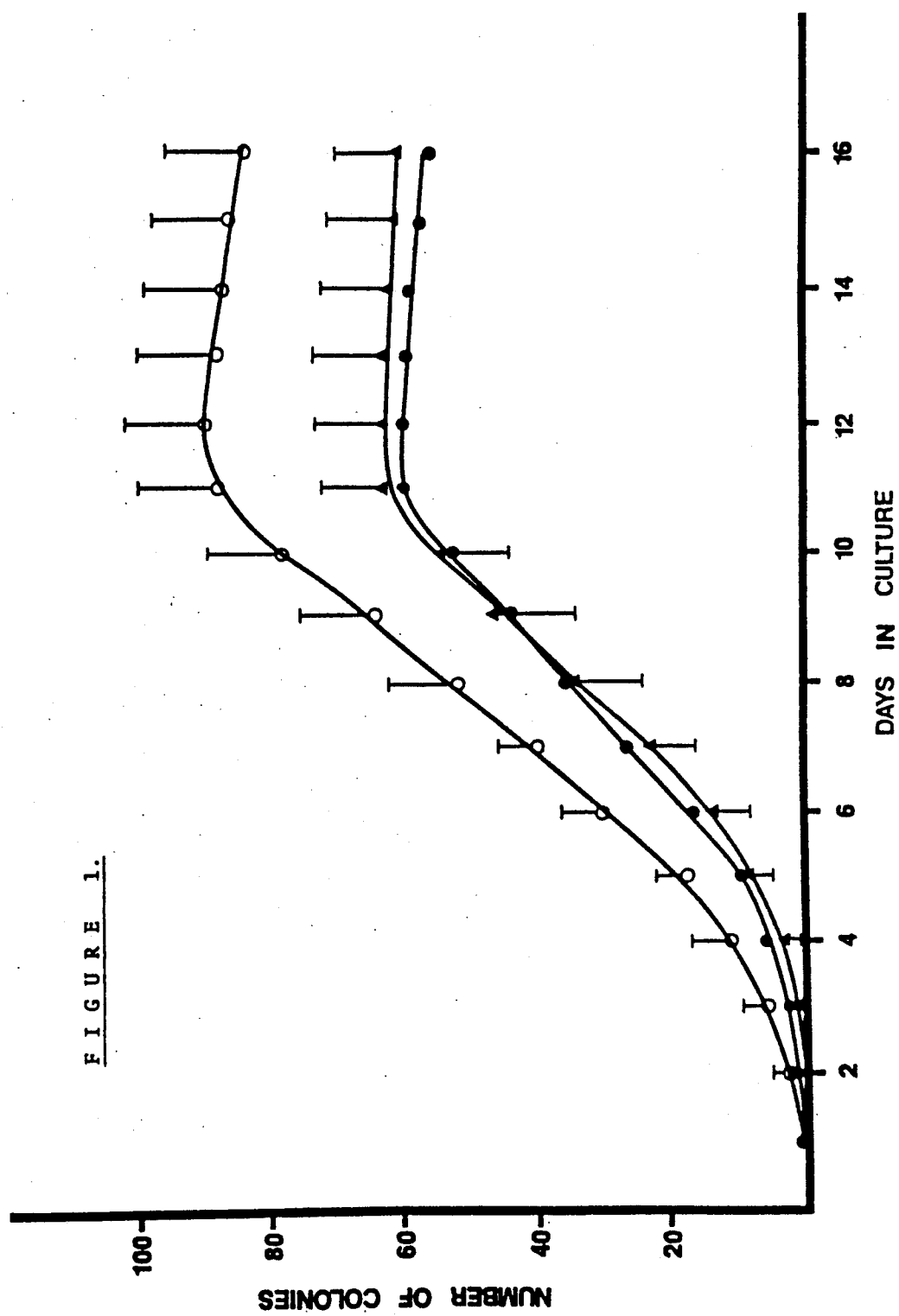
FIG. 1 depicts G-CSF activity and NGF and its proteolytically-inactive derivatives as a function of time. Two colony assay plates per marrow were employed for colony enumeration at each time point. Concentrations of all three proteins: 0.1 $\mu$g/ml ○—○ : NGF; ●—● : DIP-NGF; ∆—∆: MK-NGF. Vertical bars represent SEM (for clarity shown only for NGF and MK-NGF).
Figure 2:
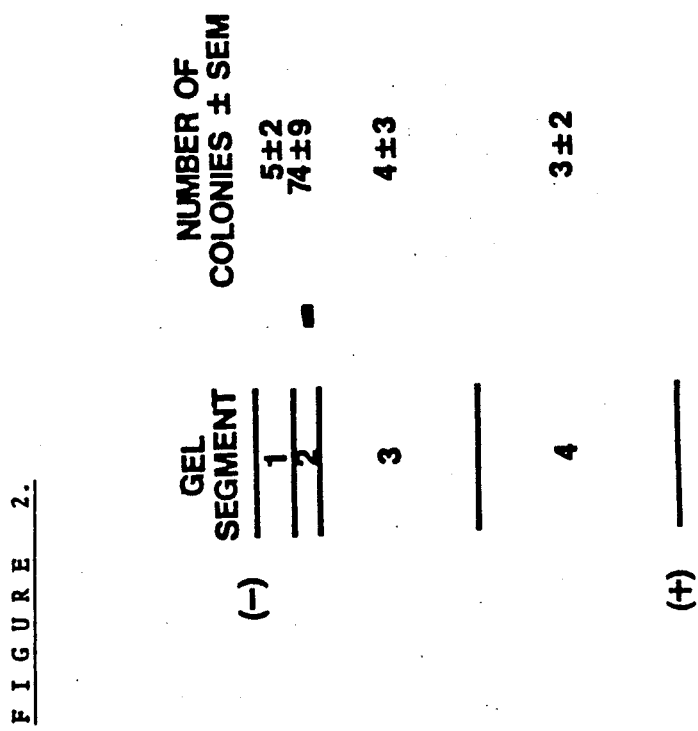
FIG. 2 sets forth the electrophoretic analysis of the G-CSF activity of NGF.
Figure 3:
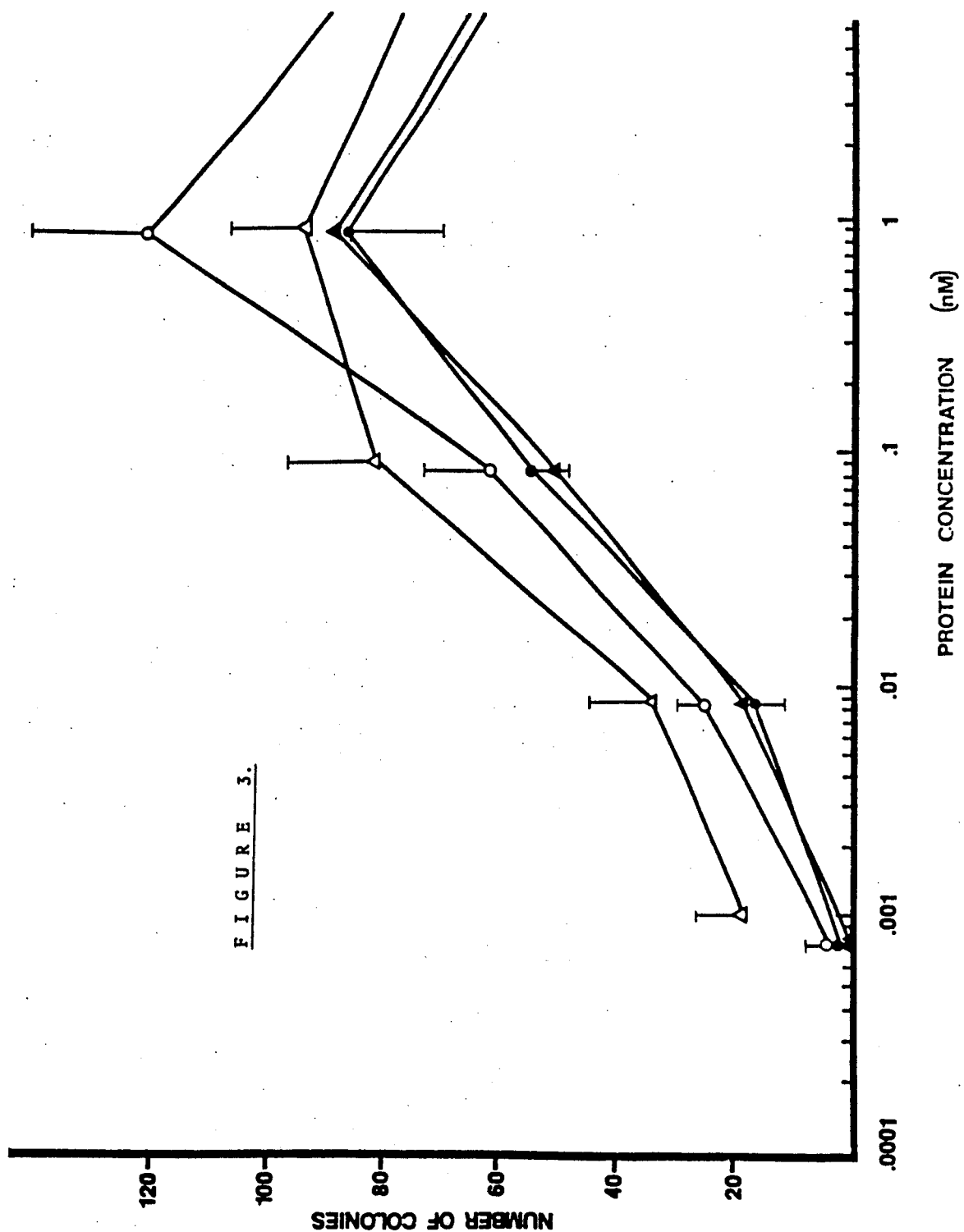
FIG. 3 depicts concentration-response profiles of NGF, DIP-NGF, MK-NGF, and the NGF $\gamma$-subunit: ○—○ : NGF; ●—● : DIP-NGF; ∆—∆: MK-NGF; ▲—▲ : $\gamma$-subunit. SEM shown for NGF and DIP-NGF.
Figure 4:
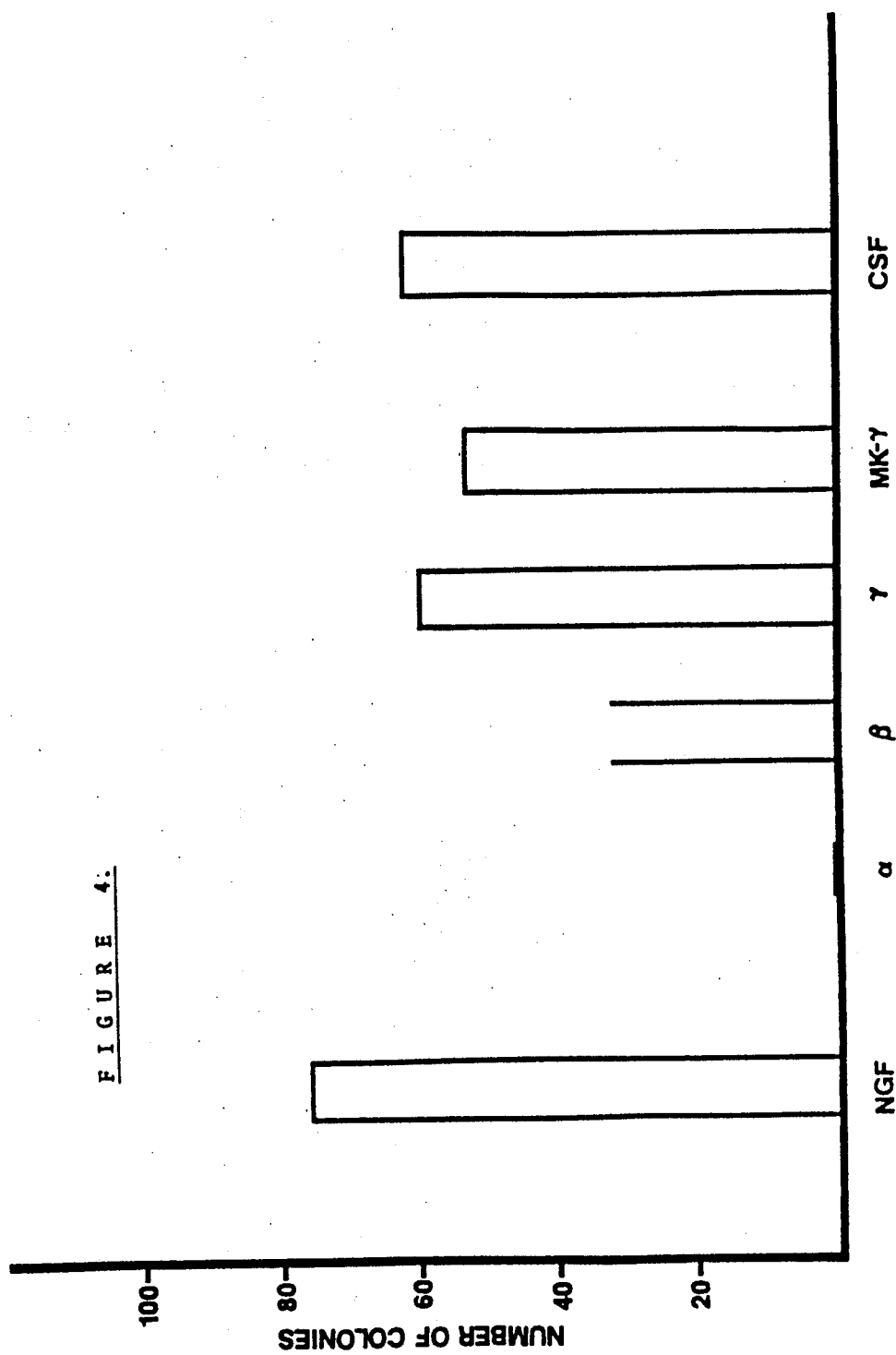
FIG. 4. depicts G-CSF activity of the three subunits of NGF.

I claim:

1. A composition for stimulating the growth of granulocytes from human bone marrow cells comprising an admixture of a granulocyte stimulating effective amount of a granulocyte colony stimulating factor selected from the group consisting of NGF and the γ-subunit of NGF, said NGF comprising a nerve growth factor having a molecular weight of about 116,000 and being derived from mouse submandibular gland or mouse saliva and a nutrient medium effective for human granulocyte proliferation.

2. The composition of claim 1 additionally containing human bone marrow.

3. The composition of claim 1 wherein said factor is NGF.

4. The composition of claim 1 wherein said factor is the γ-subunit of NGF.

5. A method for the promotion of growth of granulocytes from human bone marrow cells comprising contacting said human bone marrow cells with a granulocyte stimulating effective amount of a granulocyte colony stimulating factor selected from the group consisting of NGF and the γ-subunit of NGF, said NGF comprising a nerve growth factor having a molecular weight of about 116,000 and being derived from mouse submandibular gland or mouse saliva for a time sufficient to stimulate the proliferation of granulocytes.

6. The method of claim 5 wherein said factor is NGF.

7. The method of claim 5 wherein said factor is the γ-subunit of NGF.

* * * * *